United States Patent
Chandra et al.

(10) Patent No.: US 10,242,864 B2
(45) Date of Patent: *Mar. 26, 2019

(54) HIGH TEMPERATURE ATOMIC LAYER DEPOSITION OF SILICON OXIDE THIN FILMS

(71) Applicant: Air Products and Chemicals, Inc., Allentown, PA (US)

(72) Inventors: Haripin Chandra, San Marcos, CA (US); Meiliang Wang, Carlsbad, CA (US); Manchao Xiao, San Diego, CA (US); Xinjian Lei, Vista, CA (US); Ronald Martin Pearlstein, San Marcos, CA (US); Mark Leonard O'Neill, Queen Creek, AZ (US); Bing Han, San Marcos, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,214

(22) Filed: Aug. 26, 2016

(65) Prior Publication Data

US 2016/0365244 A1  Dec. 15, 2016
US 2017/0256399 A9  Sep. 7, 2017

Related U.S. Application Data

(63) Continuation of application No. 13/857,507, filed on Apr. 5, 2013, now Pat. No. 9,460,912.

(Continued)

(51) Int. Cl.
  *C23C 16/00* (2006.01)
  *H01L 21/02* (2006.01)
  (Continued)

(52) U.S. Cl.
  CPC .......... *H01L 21/02164* (2013.01); *C07F 7/10* (2013.01); *C23C 16/402* (2013.01);
  (Continued)

(58) Field of Classification Search
  CPC ............ C23C 16/402; C23C 16/45527; C23C 16/45553
  (Continued)

(56) References Cited

U.S. PATENT DOCUMENTS 6,992,019 B2   1/2006   Lee et al.
7,084,076 B2   8/2006   Park et al.
(Continued)

FOREIGN PATENT DOCUMENTS

EP   1785266 A1   5/2007
EP   1860690 A2   11/2007
(Continued)

OTHER PUBLICATIONS

Burton et al. J Phys. Chem. C 2009, 133 pp. 8249-8257.*
(Continued)

*Primary Examiner* — Kelly M Gambetta
(74) *Attorney, Agent, or Firm* — Joseph D. Rossi

(57) ABSTRACT

Atomic layer deposition (ALD) process formation of silicon oxide with temperature >500° C. is disclosed. Silicon precursors used have a formula of:

$$R^1R^2{}_mSi(NR^3R^4)_nX_p \qquad \text{I.}$$

wherein $R^1$, $R^2$, and $R^3$ are each independently selected from hydrogen, a linear or branched $C_1$ to $C_{10}$ alkyl group, and a $C_6$ to $C_{10}$ aryl group; $R^4$ is selected from, a linear or branched $C_1$ to $C_{10}$ alkyl group, and a $C_6$ to $C_{10}$ aryl group, a $C_3$ to $C_{10}$ alkylsilyl group; wherein $R^3$ and $R^4$ are linked to form a cyclic ring structure or $R^3$ and $R^4$ are not linked to form a cyclic ring structure; X is a halide selected from the
(Continued)

group consisting of Cl, Br and I; m is 0 to 3; n is 0, 1 or 2; and p is 0, 1 or 2 and m+n+p=3; and $$R^1R^2{}_m Si(OR^3)_n(OR^4)_q X_p \qquad \text{II.}$$

wherein $R^1$ and $R^2$ are each independently selected from hydrogen, a linear or branched $C_1$ to $C_{10}$ alkyl group, and a $C_6$ to $C_{10}$ aryl group; $R^3$ and $R^4$ are each independently selected from a linear or branched $C_1$ to $C_{10}$ alkyl group, and a $C_6$ to $C_{10}$ aryl group; wherein $R^3$ and $R^4$ are linked to form a cyclic ring structure or $R^3$ and $R^4$ are not linked to form a cyclic ring structure; X is a halide atom selected from the group consisting of Cl, Br and I; m is 0 to 3; n is 0 to 2; q is 0 to 2; p is 0 to 2; and m+n+q+p=3.

8 Claims, 2 Drawing Sheets

Related U.S. Application Data

(60) Provisional application No. 61/623,217, filed on Apr. 12, 2012.

(51) Int. Cl.
 *C23C 16/40* (2006.01)
 *C23C 16/455* (2006.01)
 *C07F 7/10* (2006.01)

(52) U.S. Cl.
 CPC .. *C23C 16/45527* (2013.01); *C23C 16/45553* (2013.01); *H01L 21/0228* (2013.01); *H01L 21/02274* (2013.01)

(58) Field of Classification Search
 USPC ............ 427/255.37, 255.29, 255.28, 255.23, 427/248.1
 See application file for complete search history.

(56) References Cited

U.S. PATENT DOCUMENTS

| 7,500,397 | B2* | 3/2009 | Weigel ............. H01L 21/02126 438/710 |
| 7,521,263 | B2 | 4/2009 | Toshiba |
| 9,460,912 | B2* | 10/2016 | Chandra ............... C23C 16/402 |
| 2005/0271813 | A1 | 12/2005 | Kher et al. |
| 2008/0124946 | A1 | 5/2008 | Xiao et al. |
| 2008/0207007 | A1 | 8/2008 | Thridandam et al. |
| 2009/0263975 | A1 | 10/2009 | Kadonaga et al. |
| 2011/0207319 | A1 | 8/2011 | Imada et al. |
| 2012/0021127 | A1 | 1/2012 | Sato et al. |
| 2013/0126986 | A1* | 5/2013 | Brodsky ........... H01L 21/28255 257/411 |

FOREIGN PATENT DOCUMENTS

| EP | 1928015 A2 | 6/2008 |
| EP | 2228465 A1 | 9/2010 |
| EP | 2363512 A1 | 9/2011 |
| EP | 2463404 A1 | 6/2012 |
| JP | 2000077399 | 3/2000 |
| JP | 2005011904 A2 | 1/2005 |
| JP | 2007005633 | 1/2007 |
| JP | 2007507902 | 3/2007 |
| JP | 2007318142 | 12/2007 |
| JP | 2008514605 | 5/2008 |
| JP | 2008135633 | 6/2008 |
| JP | 200932911 | 2/2009 |
| JP | 2009246405 A * | 10/2009 |
| JP | 2009246405 A | 10/2009 |
| JP | 2009538989 | 12/2009 |
| JP | 2010066597 | 3/2010 |
| JP | 4476880 | 6/2010 |
| JP | 2010225663 | 10/2010 |
| JP | 2010275602 | 12/2010 |
| JP | 2010539730 | 12/2010 |
| JP | 2011108737 A2 | 2/2011 |
| JP | 4836761 | 12/2011 |
| KR | 1020080076847 | 8/2008 |
| WO | 2005034195 A2 | 4/2005 |
| WO | 2007002040 A2 | 1/2007 |
| WO | 2007139379 | 12/2007 |
| WO | 2008048862 A2 | 4/2008 |
| WO | 2009039251 A1 | 3/2009 |
| WO | 2010064306 | 6/2010 |

OTHER PUBLICATIONS

Burton, B. B. et al., "SiO2 Atomic Layer Deposition Using Tris(dimethylamino)silane and Hydrogen Peroxide Studied by in Situ Transmission FTIR Spectroscopy", Journal of Physical Chemistry C, vol. 113, No. 19, pp. 8249-8257, Apr. 17, 2009.
O'Neill M L et al., "Impact of Aminosilane Precursor Structure on Silicon Oxides by Atomic Layer Deposition," The Electrochemical Society Interface, vol. 20, No. 4, 2011, pp. 33-37.
Iwanaga K et al., "Development of Novel Silicon Precursors for Low-Temperature CVD/ALD Processes," ECS Transactions, Atomic Layer Deposition Applications 7—220th ECS Meeting, Oct. 9-Oct. 14, 2011, Boston, MA, vol. 41, Oct. 2011 (Oct. 2011), pp. 211-218.
Wolf, S., Silicon Processing for the VLSI Era vol. 1—Process Technology, Lattice Press, CA, 1986, 208-209.

* cited by examiner

HIGH TEMPERATURE ATOMIC LAYER DEPOSITION OF SILICON OXIDE THIN FILMS

CROSS REFERENCE TO RELATED APPLICATIONS

This patent application is a continuation application of U.S. Ser. No. 13/857,507, filed on Apr. 5, 2013, which, in turn claims the benefit of priority under 35 U.S.C. § 119(e) of U.S. provisional patent application Ser. No. 61/623,217, filed on Apr. 12, 2012, the disclosures of which are incorporated herein by reference in their entirety.

BACKGROUND OF THE INVENTION

Described herein is a composition and method for the formation of a silicon oxide film. More specifically, described herein is a composition and method for formation of a silicon oxide film at one or more deposition temperatures of about 500° C. or greater and using an atomic layer deposition (ALD) process.

Thermal oxidation is a process commonly used to deposit high purity and highly conformal silicon oxide films such as silicon dioxide ($SiO_2$) in semiconductor applications. However, the thermal oxidation process has a very low deposition rate, e.g., than 0.03 Å/s at 700° C. which makes it impractical for high volume manufacturing processes (see, for example, Wolf, S., "Silicon Processing for the VLSI Era Vol. 1—Process Technology", Lattice Press, CA, 1986).

Atomic Layer Deposition (ALD) and Plasma Enhanced Atomic Layer Deposition (PEALD) are processes used to deposit silicon dioxide ($SiO_2$) conformal film at low temperature (<500° C.). In both ALD and PEALD processes, the precursor and reactive gas (such as oxygen or ozone) are separately pulsed in certain number of cycles to form a monolayer of silicon dioxide ($SiO_2$) at each cycle. However, silicon dioxide ($SiO_2$) deposited at low temperatures using these processes may contain levels of impurities such as carbon (C), nitrogen (N), or both which are detrimental to semiconductor applications. To remedy this, one possible solution would be to increase deposition temperature such as 500° C. or greater. However, at these higher temperatures, conventional precursors employed by semi-conductor industries tend to self-react, thermally decompose, and deposit in CVD mode rather than ALD mode. The CVD mode deposition has reduced conformality compared to ALD deposition, especially in high aspect ratio structure in semiconductor applications. In addition, the CVD mode deposition has less control of film or material thickness than the ALD mode deposition.

JP2010275602 and JP2010225663 disclose the use of a raw material to form a Si containing thin film such as, silicon oxide by a chemical vapor deposition (CVD) process at a temperature range of from 300-500° C. The raw material is an organic silicon compound, represented by formula: (a)$HSi(CH_3)(R^1)(NR^2R^3)$, wherein $R^1$ represents $NR^4R^5$ or a 1C-5C alkyl group; $R^2$ and $R^4$ each represent a 1C-5C alkyl group or hydrogen atom; and $R^3$ and $R^5$ each represent a 1C-5C alkyl group); or (b) $HSiCl(NR^1R^2)(NR^3R^4)$, wherein $R^1$ and $R^3$ independently represent an alkyl group having 1 to 4 carbon atoms, or a hydrogen atom; and $R^2$ and $R^4$ independently represent an alkyl group having 1 to 4 carbon atoms. The organic silicon compounds contained H—Si bonds U.S. Pat. No. 7,084,076 ("the '076 Patent") discloses a halogenated siloxane such as hexachlorodisiloxane (HCDSO) that is used in conjunction with pyridine as a catalyst for ALD deposition below 500° C. to form silicon dioxide.

U.S. Pat. No. 6,992,019 ("the '019 Patent") discloses a method for catalyst-assisted atomic layer deposition (ALD) to form a silicon dioxide layer having superior properties on a semiconductor substrate by using a first reactant component consisting of a silicon compound having at least two silicon atoms, or using a tertiary aliphatic amine as the catalyst component, or both in combination, together with related purging methods and sequencing. The precursor used is hexachlorodisilane. The deposition temperature is between 25-150° C.

Thus, there is a need to develop a process for forming a high quality, low impurity, high conformal silicon oxide film using an atomic layer deposition (ALD) process or an ALD-like process, such as without limitation a cyclic chemical vapor deposition process, to replace thermal-based deposition processes. Further, it may be desirable to develop a high temperature deposition (e.g., deposition at one or more temperatures of 500° C.) to improve one or more film properties, such as purity and/or density, in an ALD or ALD-like process.

BRIEF SUMMARY OF THE INVENTION

Described herein is a process for the deposition of a silicon oxide material or film at high temperatures, e.g., at one or more temperatures of 500° C. or greater, in an atomic layer deposition (ALD) or an ALD-like process.

One embodiment provides a process to deposit silicon oxide comprising steps of:
a. providing a substrate in a reactor;
b. introducing into the reactor at least one silicon precursor;
c. purging reactor with purge gas;
d. introducing an oxygen source into the reactor; and
e. purging reactor with purge gas; and
where steps b through e are repeated until a desired thickness of silicon oxide is deposited; and wherein the process is conducted at one or more temperatures ranging from 500 to 800° C. and at one or more pressure ranging from 50 miliTorr (mT) to 760 Torr.

Another embodiment provides a process to deposit silicon oxide comprising steps of:
a. providing a substrate in a reactor;
b. introducing into the reactor at least one silicon precursor;
c. purging reactor with purge gas;
d. introducing an oxygen source into the reactor;
e. purging reactor with purge gas;
f. introducing water vapor or hydroxyl source into the reactor;
g. purging reactor with purge gas; and
where steps b through g are repeated until a desired thickness of silicon oxide is deposited; and wherein the process is conducted at one or more temperatures ranging from 500 to 800° C. and at one or more pressure ranging from 50 miliTorr (mT) to 760 Torr. In this or other embodiments, the oxygen source is selected from the group consisting of oxygen, oxygen plasma, water vapor, water vapor plasma, hydrogen peroxide, nitrogen oxides, and ozone.

The at least one silicon precursor described herein is selected from the group consisting of:

$$R^1R^2{}_mSi(NR^3R^4)_nX_p \qquad \qquad \text{I.}$$

wherein $R^1$, $R^2$, and $R^3$ are each independently selected from hydrogen, a linear or branched $C_1$ to $C_{10}$ alkyl group, and a $C_6$ to $C_{10}$ aryl group; $R^4$ is selected from hydrogen, a linear or branched $C_1$ to $C_{10}$ alkyl group, and a $C_6$ to $C_{10}$ aryl group, a $C_3$ to $C_{10}$ alkylsilyl group; wherein $R^3$ and $R^4$ are linked to form a cyclic ring structure or $R^3$ and $R^4$ are not linked to form a cyclic ring structure; X is a halide selected from the group consisting of Cl, Br and I: m is 0 to 3; n is 0, 1 or 2; and p is 0, 1 or 2 and m+n+p=3; and $$R^1R^2{}_mSi(OR^3)_n(OR^4)_qX_p \qquad \text{II.}$$

wherein $R^1$ and $R^2$ are each independently selected from hydrogen, a linear or branched $C_1$ to $C_{10}$ alkyl group, and a $C_6$ to $C_{10}$ aryl group; $R^3$ and $R^4$ are each independently selected from a linear or branched $C_1$ to $C_{10}$ alkyl group, and a $C_6$ to $C_{10}$ aryl group; wherein $R^3$ and $R^4$ are linked to form a cyclic ring structure or $R^3$ and $R^4$ are not linked to form a cyclic ring structure; X is a halide atom selected from the group consisting of Cl, Br and I; m is 0 to 3; n is 0 to 2; q is 0 to 2; p is 0 to 2; and m+n+q+p=3.

In one or more embodiments described above, the purge gas is selected from the group consisting of nitrogen, helium and argon.

In one or more embodiments described above, the oxygen source is selected from the group consisting of oxygen, oxygen plasma, water vapor, water vapor plasma, hydrogen peroxide, nitrous oxide, and ozone and combination thereof.

DETAILED DESCRIPTION OF THE INVENTION

Figure 1:
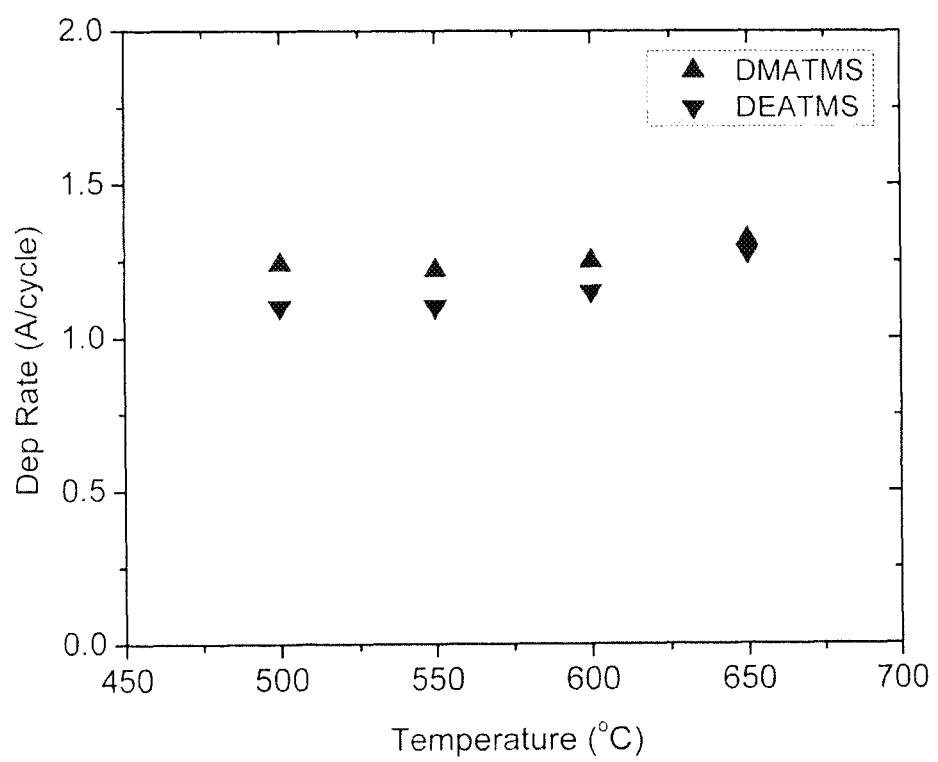
FIG. 1 shows the deposition rate of dimethylaminotrimethylsilane (DMATMS) and diethylaminotrimethylsilane (DEAMTS) as function of temperatures, suggesting both precursors can have an ALD window up to 650° C.

Described herein are compositions and processes related to the formation of a silicon oxide containing film, such as a silicon oxynitride film, a stoichiometric or non-stoichiometric silicon oxide film, a silicon oxide film or combinations, thereof with one or more temperatures, of 500° C. or greater, in an atomic layer deposition (ALD) or in an ALD-like process, such as without limitation a cyclic chemical vapor deposition process (CCVD).

Typical ALD processes in the prior art uses an oxygen source, or oxidizer such as oxygen, oxygen plasma, water vapor, water vapor plasma, hydrogen peroxide, or ozone source directly to form $SiO_2$ at process temperatures ranging from 25 to 500° C. The deposition steps comprises of.
  a. providing a substrate in a reactor
  b. introducing into the reactor a silicon precursor
  c. purging reactor with purge gas
  d. introducing oxygen source into the reactor; and
  e purging reactor with purge gas.

In the prior art process, steps b through e are repeated until desired thickness of film is deposited.

It is believed that high temperature process, above 500° C., may yield better film quality in term of film purity and density. ALD process provides good film step coverage. However, typical organosilicon precursors used in ALD or PEALD only deposit films in ALD mode within a certain temperature range. When temperature is higher than this range, thermal decomposition of the precursor occurs which causes either gas phase reaction or continuous substrate surface reaction which changes the deposition process to CVD mode, rather than the desired ALD mode.

Not being bound by theory, for ALD or ALD-like deposition process at one or more temperatures greater than 500° C., the silicon precursor molecules described herein should have at least one anchoring functionality, which reacts with certain reactive sites on the substrate surface to anchor a monolayer of silicon species. The anchoring functionalities can be selected from a halide (Cl, Br, I) group, an amino group, or an alkoxy group, preferably an amino-group such as dimethylamino or diethylamino groups. The silicon precursor should also have a passive functionality in that it is chemically stable as to prevent further surface reaction, leading to a self-limiting process. The passivating functionality is selected from different alkyl groups such as methyl, ethyl, phenyl groups, preferably a methyl group. The remaining groups on the surface can then be oxidized to form a Si—O—Si linkage as well as hydroxyl groups. In addition, hydroxyl sources such as $H_2O$ or water plasma can also be introduced into the reactor to form more hydroxyl groups as reactive sites for the next ALD cycle as demonstrated in the following Scheme 1.

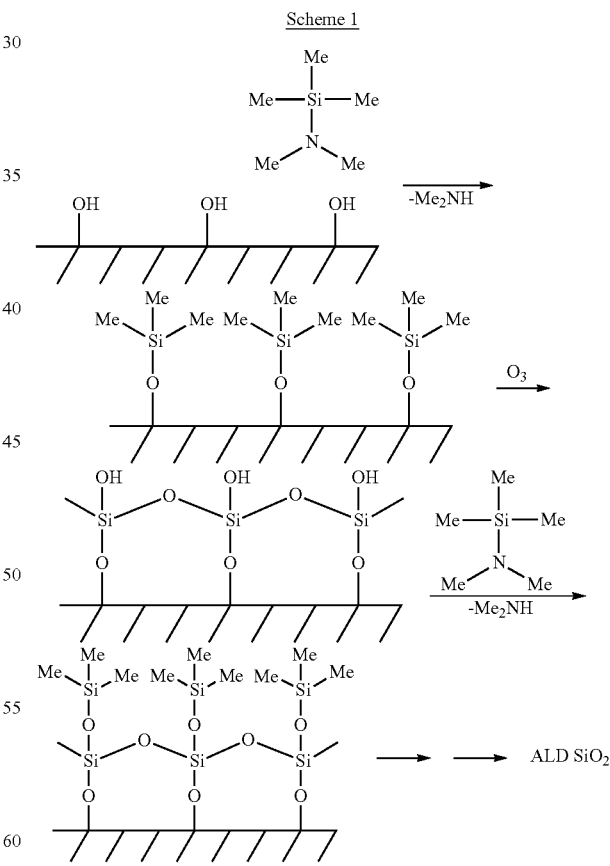

In one embodiment, the at least one silicon precursor described herein is a compound having the following formula I:

$$R^1R^2{}_mSi(NR^3R^4)_nX_p \qquad \text{I.}$$

wherein $R^1$, $R^2$, and $R^3$ are each independently selected from hydrogen, a linear or branched $C_1$ to $C_{10}$ alkyl group, and a $C_6$ to $C_{10}$ aryl group; $R^4$ is selected from, a linear or branched $C_1$ to $C_{10}$ alkyl group, and a $C_6$ to $C_{10}$ aryl group, a $C_3$ to $C_{10}$ alkylsilyl group; wherein $R^3$ and $R^4$ are linked to form a cyclic ring structure or $R^3$ and $R^4$ are not linked to form a cyclic ring structure; X is a halide selected from the group consisting of Cl, Br and I; m is 0 to 3; n is 0 to 2; and p is 0 to 2 and m+n+p=3 Examples of precursors having Formula I include are but not limited to: diethylaminotrimethylsilane, dimethylaminotrimethylsilane, ethylmethylaminotrimethylsilane, diethylaminotriethylsilane, dimethylaminotriethylsilane, ethylmethylaminotriethylsilane, t-butylaminotriethylsilane, iso-propylaminotriethylsilane, di-isopropylaminotriethylsilane, pyrrolidinotriethylsilane, t-butylaminotrimethylsilane, iso-propylaminotrimethylsilane, di-isopropylaminotrimethylsilane, pyrrolidinotrimethylsilane, diethylaminodimethylsilane, dimethylaminodimethylsilane, ethylmethylaminodimethylsilane, t-butylaminodimethylsilane, iso-propylaminodimethylsilane, di-isopropylaminodimethylsilane, pyrrolidinodimethylsilane, diethylaminodiethylsilane, dimethylaminodiethylsilane, ethylmethylaminodiethylsilane, t-butylaminodiethylsilane, iso-propylaminodiethylsilane, di-isopropylaminodiethylsilane, pyrrolidonodiethylsilane, bis(diethylamino)dimethylsilane, bis(dimethylamino)dimethylsilane, bis(ethylmethylamino)dimethylsilane, bis(di-isopropyllamino)dimethylsilane, bis(iso-propylamino)dimethylsilane, bis(tert-butylamino)dimethylsilane, dipyrrolidinodimethylsilane, bis(diethylamino)diethylsilane, bis(dimethylamino)diethylsilane, bis(ethylmethylamino)diethylsilane, bis(di-isopropyllamino)diethylsilane, bis(iso-propylamino)diethylsilane, bis(tert-butylamino) diethylsilane, dipyrrolidinodiethylsilane, bis(diethylamino) methylvinylsilane, bis(dimethylamino)methylvinylsilane bis(ethylmethylamino)methylvinylsilane, bis(di-isopropyl-lamino)methylvinylsilane, bis(iso-propylamino)methylvinylsilane, bis(tert-butylamino)methylvinylsilane, dipyrrolidinomethylvinylsilane, 2,6-dimethylpiperidinomethylsilane, 2,6-dimethylpiperidinodimethylsilane, 2,6-dimethylpiperidinotrimethylsilane, tris(dimethylamino)phenylsilane, tris (dimethylamino)methylsilane, tris(dimethylamino)ethylsilane, and tris(dimethylamino)chlorosilane.

Further examples of Group I silicon precursors wherein $R^4$ in Formula I is a $C_3$ to $C_{10}$ alkylsilyl group include but are not limited to: 1,1,1,3,3,3-hexamethyldisilazane, 1,1,1,3,3,3-hexaethyldisilazane, 1,1,3,3-tetramethyldisilazane, 1,1,3,3-tetraethyldisilazane, 1,1,1,2,3,3,3-heptamethyldisilazane, 1,1,1,3,3,3-hexaethyl-2-methyldisilazane, 1,1,2,3,3-pentamethyldisilazane, 1,1,3,3-tetraethyl-2-methyldisilazane, 1,1,1,3,3,3-hexamethyl-2-ethyldisilazane, 1,1,1,2,3,3,3-heptaethyldisilazane, 1,1,3,3-tetramethyl-2-ethyldisilazane, 1,1,2,3,3-pentaethyldisilazane, 1,1,1,3,3,3-hexamethyl-2-isopropyldisilazane, 1,1,1,3,3,3-hexaethyl-2-isopropyldisilazane, 1,1,3,3-tetramethyl-2-isopropyldisilazane, and 1,1,3,3-tetraethyl-2-isopropyldisilazane.

In a further embodiment, the at least one silicon precursor described herein is a compound having the following Formula II:

wherein $R^1$ and $R^2$ are each independently selected from hydrogen, a linear or branched $C_1$ to $C_{10}$ alkyl group, and a $C_6$ to $C_{10}$ aryl group; $R^3$ and $R^4$ are each independently selected from a linear or branched $C_1$ to $C_{10}$ alkyl group, and a $C_6$ to $C_{10}$ aryl group; wherein $R^3$ and $R^4$ are linked to form a cyclic ring structure or $R^3$ and $R^4$ are not linked to form a cyclic ring structure; X is a halide atom selected from the group consisting of Cl, Br and I; m is 0 to 3; n is 0 to 2; q is 0 to 2 and p is 0 to 2 and m+n+q+p=3. Examples of such Group II silicon precursors include but are not limited to: methoxytrimethylsilane, ethoxytrimethylsilane, iso-propoxytrimethylsilane, tert-butoxytrimethylsilane, tert-pentoxytrimethylsilane, phenoxytrimethylsilane, acetoxytrimethylsilane, methoxytriethylsilane, ethoxytriethylsilane, iso-propoxytriethylsilane, tert-butoxytriethylsilane, tert-pentoxytriethylsilane, phenoxytriethylsilane, acetoxytriethylsilane, methoxydimethylsilane, ethoxydimethylsilane, iso-propoxydimethylsilane, tert-butoxydimethylsilane, tert-pentoxydimethylsilane, phenoxydimethylsilane, acetoxydimethylsilane, methoxydimethylphenylsilane, ethoxydimethylphenylsilane, iso-propoxydimethylphenylsilane, tert-butoxydimethylphenylsilane, tert-pentoxydimethylphenylsilane, phenoxydimethylphenylsilane, acetoxydimethylphenylsilane, dimethoxydimethylsilane, diethoxydimethylsilane, di-isopropoxydimethylsilane, di-t-butoxydimethylsilane, diacytoxydimethylsilane, dimethoxydiethylsilane, diethoxydiethylsilane, di-isopropoxydiethylsilane, di-t-butoxydiethylsilane, diacytoxydiethylsilane, dimethoxydi-isopropylsilane, diethoxydi-isopropylsilane, di-isopropoxydi-isopropylsilane, di-t-butoxydi-isopropylsilane, diacytoxydi-isopropylsilane, dimethoxymethylvinylsilane, diethoxymethylvinylsilane, di-isopropoxymethylvinylsilane, di-t-butoxymethylvinylsilane, diacytoxymethylvinylsilane, 1,1,3,4-tetramethyl-1-sila-2,5-dioxacyclopentane, and 1,1,3,3,4,4-hexamethyl-1-sila-2,5-dioxacyclopentane.

In the formulas above and throughout the description, the term "alkyl" denotes a linear or branched functional group having from 1 to 10, 3 to 10, or 1 to 6 carbon atoms. Exemplary linear alkyl groups include, but are not limited to, methyl, ethyl, propyl, butyl, pentyl, and hexyl groups. Exemplary branched alkyl groups include, but are not limited to, isopropyl, isobutyl, sec-butyl, tert-butyl, iso-pentyl, tert-pentyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto. The alkyl group may be saturated or, alternatively, unsaturated.

In the formulas above and throughout the description, the term "aryl" denotes an aromatic cyclic functional group having from 3 to 10 carbon atoms, from 5 to 10 carbon atoms, or from 6 to 10 carbon atoms. Exemplary aryl groups include, but are not limited to, phenyl, benzyl, chlorobenzyl, tolyl, and o-xylyl.

In the formulas above and throughout the description, the term "alkoxy" denotes an alkyl group which is linked to an oxygen atom (e.g., R—O) and may have from 1 to 12 or from 1 to 6 carbon atoms. Exemplary alkoxy groups include, but are not limited to, methoxy, ethoxy, propoxy, iso-propoxy, butoxy, isobutoxy, sec-butoxy, tert-butoxy, pentoxy, tert-pentoxy, isopentoxy, neo-pentoxy, hexoxy, and 2-ethylhexoxy. In the formulas above and throughout the description, the term "amino" denotes an alkyl or aromatic group which is linked to a nitrogen atom (e.g., $NR^3R^4$ defined as above) and may have from 1 to 12 or from 1 to 6 carbon atoms. Exemplary amino groups include, but are not limited to, dimethylamino, diethylamino, tert-butylamino, cyclohexylamino, piperidino, alkyl substituted piperidino (for example 2,6-dimethylpiperdino), pyrrolidino, alkyl substituted pyrrolidino (for example 2,5-dimethylpyrrolidino), pyrrolyl, alkyl-substituted pyrrolyl, imidazolyl, and alkyl substituted imidazolyl groups.

In the formulas above and through the description, the term "unsaturated" as used herein means that the functional group, substituent, ring or bridge has one or more carbon double or triple bonds. An example of an unsaturated ring can be, without limitation, an aromatic ring such as a phenyl ring. The term "saturated" means that the functional group, substituent, ring or bridge does not have one or more double or triple bonds.

In the formulas above and throughout the description, the term "alkylsilyl" denotes a linear or branched functional group having from 3 to 10. Exemplary alkylsilyl groups include, but are not limited to, trimethylsilyl, triethylsilyl, dimethylsilyl, diethylsilyl, and dimethylethylsilyl.

In certain embodiments, substituents $R^3$ and $R^4$ in Formula I or Formula II can be linked together to form a ring structure. As the skilled person will understand, where $R^3$ and $R^4$ are linked together to form a ring $R^3$ will include a bond for linking to $R^4$ and vice versa. In these embodiments, the ring structure can be unsaturated such as, for example, a cyclic alkyl ring, or saturated, for example, an aryl ring. Further, in these embodiments, the ring structure can also be substituted or substituted. Exemplary cyclic ring groups include, but are not limited to, pyrrolidino, piperidino, and 2,6-dimethylpiperidino groups. In other embodiments, however, substituent $R^3$ and $R^4$ are not linked.

In certain embodiments, the silicon films deposited using the methods described herein are formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), $N_2O$, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 standard cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited dielectric film.

In certain embodiments, the silicon oxide films further comprises nitrogen. In these embodiments, the films are deposited using the methods described herein and formed in the presence of nitrogen-containing source. A nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting dielectric film.

Energy is applied to the at least one of the silicon precursor, oxygen containing source, or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The at least one silicon precursors may be delivered to the reaction chamber such as a cyclic CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the at least one silicon precursor precursor(s) having Formula I or II is used in a composition comprising a solvent and an at least one silicon precursor having Formula I or II described herein, the solvent or mixture thereof selected does not react with the silicon precursor. The amount of solvent by weight percentage in the composition ranges from 0.5% by weight to 99.5% or from 10% by weight to 75%. In this or other embodiments, the solvent has a boiling point (b.p.) similar to the b.p. of the at least one silicon precursor of Formula I or Formula II or the difference between the b.p. of the solvent and the b.p. of the t least one silicon precursor of Formula I or Formula II is 40° C. or less, 30° C. or less, or 20° C. or less, or 10° C. or less. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkane (such as octane, nonane, dodecane, ethylcyclohexane), an aromatic hydrocarbon (such as toluene, mesitylene), a tertiary aminoether (such as bis(2-dimethylaminoethyl) ether), or mixtures thereof.

As previously mentioned, the purity level of the at least one silicon precursor of Formula I or Formula II is sufficiently high enough to be acceptable for reliable semiconductor manufacturing. In certain embodiments, the at least one silicon precursor of Formula I or Formula II described herein comprise less than 2% by weight, or less than 1% by weight, or less than 0.5% by weight of one or more of the following impurities: free amines, free halides or halogen ions, and higher molecular weight species. Higher purity levels of the silicon precursor described herein can be obtained through one or more of the following processes: purification, adsorption, and/or distillation.

In one embodiment of the method described herein, a cyclic deposition process such as ALD-like, ALD, or PEALD may be used wherein the deposition is conducted using the at least one silicon precursor of Formula I or Formula II and an oxygen source. The ALD-like process is defined as a cyclic CVD process but still provides high conformal silicon oxide films.

In certain embodiments, the gas lines connecting from the precursor canisters to the reaction chamber are heated to one or more temperatures depending upon the process requirements and the container of the at least one silicon precursor of Formula I or Formula II is kept at one or more temperatures for bubbling. In other embodiments, a solution comprising the t least one silicon precursor of Formula I or Formula II is injected into a vaporizer kept at one or more temperatures for direct liquid injection.

A flow of argon and/or other gas may be employed as a carrier gas to help deliver the vapor of the at least one silicon precursor of Formula I or Formula II to the reaction chamber during the precursor pulsing. In certain embodiments, the reaction chamber process pressure is about 1 Torr.

In a typical ALD or an ALD-like process such as a CCVD process, the substrate such as a silicon oxide substrate is heated on a heater stage in a reaction chamber that is exposed to the silicon precursor initially to allow the complex to chemically adsorb onto the surface of the substrate.

A purge gas such as argon purges away unabsorbed excess complex from the process chamber. After sufficient purging, an oxygen source may be introduced into reaction chamber to react with the absorbed surface followed by another gas purge to remove reaction by-products from the chamber. The process cycle can be repeated to achieve the desired film thickness. In some cases, pumping can replace a purge with inert gas or both can be employed to remove unreacted silicon precursors.

In this or other embodiments, it is understood that the steps of the methods described herein may be performed in a variety of orders, may be performed sequentially, may be performed concurrently (e.g., during at least a portion of another step), and any combination thereof. The respective step of supplying the precursors and the oxygen source gases may be performed by varying the duration of the time for supplying them to change the stoichiometric composition of the resulting dielectric film.

One particular embodiment of the method described herein to deposit a silicon oxide film on a substrate comprises the following steps:
a. providing a substrate in a reactor
b. introducing into the reactor at least one silicon precursor described herein having formula I, II, or both
c. purging reactor with purge gas
d. introducing oxygen source into the reactor and
e. purging reactor with purge gas
wherein steps b through e are repeated until a desired thickness of the silicon oxide film is deposited.

In one particular embodiment of the method and composition described herein, the silicon precursor is a compound having the following Formula I:

$$R^1R^2_mSi(NR^3R^4)_nX_p \qquad I.$$

wherein $R^1$ is a methyl (Me) group, $R^2$ is a Me group, m=2, n=1, p=0, $R^3$ is selected from hydrogen, a linear or branched $C_1$ to $C_{10}$ alkyl group, and a $C_6$ to $C_{10}$ aryl group; $R^4$ is selected from, a linear or branched $C_1$ to $C_{10}$ alkyl group, and a $C_6$ to $C_{10}$ aryl group, a $C_3$ to $C_{10}$ alkylsilyl group; wherein $R^3$ and $R^4$ are linked to form a cyclic ring structure or $R^3$ and $R^4$ are not linked to form a cyclic ring structure. Table 1 below shows structures of exemplary silicon precursors having an anchoring functionality selected from a halide atom, an amine group, or an alkoxy group and having a passivating functionally selected from an alkyl group which is preferably a methyl or Me group. Not bound by theory, it is believed that the Si-Me groups are stable at temperatures higher than 500° C. and provide a passivation functionality to prevent further surface reaction, leading to a self-limiting ALD or ALD-like process.

TABLE 1

Silicon precursors having at least one anchoring functionality and at least one passivating functionality (e.g., 3 methyl groups).

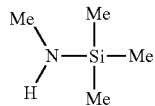

Methylaminotrimethylsilane

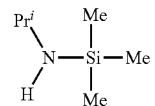

Iso-propylaminotrimethylsilane

TABLE 1-continued

Silicon precursors having at least one anchoring functionality and at least one passivating functionality (e.g., 3 methyl groups).

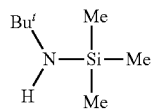

Tert-butylaminotrimethylsilane

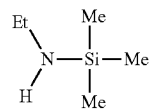

Ethylaminotrimethylsilane

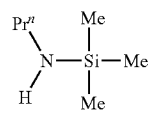

Normal-propylaminotrimethylsilane

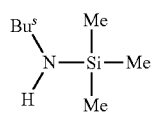

Iso-butylaminotrimethylsilane

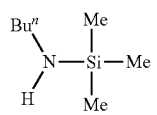

Normal-butylaminotrimethylsilane

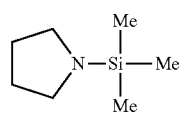

Pyrrolidinotrimethylsilane

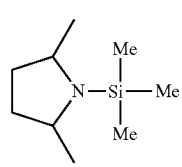

2,5-dimethylpyrrolidinotrimethylsilane

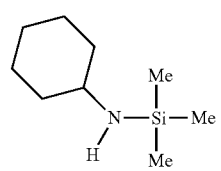 [SMILES: C[Si](C)(C)NC1CCCCC1]

Cyclohexaminotrimethylsilane

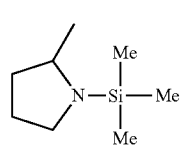

2-methylpyrrolidinotrimethylsilane

TABLE 1-continued

Silicon precursors having at least one anchoring functionality and at least one passivating functionality (e.g., 3 methyl groups).

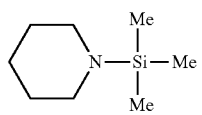

Piperidinotrimethylsilane

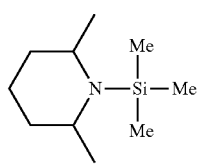

2,6-dimethylpiperidinotrimethylsilane

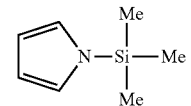

Pyrrolyltrimethylsilane

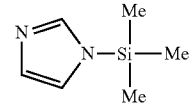

Imidazolyltrimethylsilane

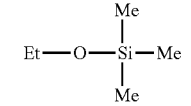

Ethoxytrimethylsilane

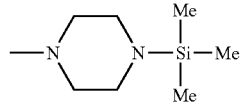

1-methylpiperazinotrimethylsilane

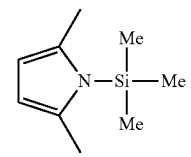

2,5-dimethylpyrrolyltrimethylsilane

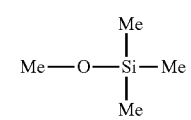

Methoxytrimethylsilane

TABLE 1-continued

Silicon precursors having at least one anchoring functionality and at least one passivating functionality (e.g., 3 methyl groups).

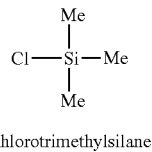

Chlorotrimethylsilane

Another embodiment of the method described herein introduces a hydroxyl or OH source such as $H_2O$ vapor after the oxidizing step. The goal in this embodiment to repopulate the anchoring functionality or reactive sites for silicon precursor which anchor on the surface to form the monolayer. The deposition steps are comprised of:

a. providing a substrate in a reactor
b. introducing into the reactor one silicon precursor described above
c. purging reactor with purge gas
d. introducing oxidizer into the reactor
e. purging reactor with purge gas
f. introducing water vapor or hydroxyl source into the reactor; and
g. purging reactor with purge gas wherein steps b through g are repeated until desired thickness is deposited.

In an alternative embodiment of the method described herein, the deposition steps are comprised of:

a. providing a substrate in a reactor
b. introducing into the reactor one silicon precursor described above
c. purging reactor with purge gas
d. introducing oxygen source into the reactor
e. purging reactor with purge gas
f. introducing water vapor or OH source into the reactor; and
g. purging reactor with purge gas wherein steps b through i are repeated until desired thickness is deposited.

Yet another embodiment employs hydrogen peroxide or oxygen plasma to remove a passivating functionality or group such as methyl. The deposition steps are as follows:

a. providing a substrate in a reactor
b. introducing into the reactor one silicon precursor described above
c. purging reactor with purge gas
d. introducing ozone, hydrogen peroxide or oxygen plasma into the reactor; and
e. purging reactor with purge gas wherein steps b through e are repeated until desired thickness is deposited Process temperature for the method described herein are one or more temperatures ranging from 500° C. to 1000° C.; or 500° C. to 750° C.; or 600° C. to 750° C.; or 600° C. to 800° C.

Deposition pressure ranges are one or more pressures ranging from 50 miliTorr (mT) to 760 Torr, or from 500 mT-100 Torr. Purge gas can be selected from inert gas such as nitrogen, helium or argon. Oxidizer is selected from oxygen, peroxide, ozone or molecular oxygen from plasma process.

EXAMPLES

Example 1: Atomic Layer Deposition of Silicon Oxide Films with Dimethylaminotrimethylsilane Atomic layer deposition of silicon oxide films were conducted using the following precursors: dimethylaminotrimethylsilane (DMATMS). The depositions were performed on a laboratory scale ALD processing tool. The silicon precursor was delivered to the chamber by vapor draw. All gases (e.g., purge and reactant gas or precursor and oxygen source) were preheated to 100° C. prior to entering the deposition zone. Gases and precursor flow rates were controlled with ALD diaphragm valves with high speed actuation. The substrates used in the deposition were 12 inch long silicon strips. A thermocouple attached on the sample holder to confirm substrate temperature. Depositions were performed using ozone as oxygen source gas. Deposition parameters are provided in Table I.

TABLE I

Process for Atomic Layer Deposition of Silicon Oxide Films with Ozone Using DMATMS

| Step 1 | 6 sec | Evacuate reactor | <100 mT |
|---|---|---|---|
| Step 2 | Variable | Dose Silicon precursor | Reactor pressure typically <2 Torr |
| Step 3 | 6 sec | Purge reactor with nitrogen | Flow 1.5 slpm $N_2$ |
| Step 4 | 6 sec | Evacuate reactor | <100 mT |
| Step 5 | 4 sec | Dose Ozone, 16-20% wt | |
| Step 6 | 6 sec | Purge reactor with nitrogen | Flow 1.5 slpm $N_2$ |

Steps 2 to 6 are repeated until a desired thickness is reached. Thickness and refractive indices of the films were measured using a FilmTek 2000SE ellipsometer by fitting the reflection data from the film to a pre-set physical model (e.g., the Lorentz Oscillator model). Wet etch rate was performed using 1% solution of 49% hydrofluoric (HF) acid in deionized water. Thermal oxide wafers were used as reference for each batch to confirm solution concentration. Typical thermal oxide wafer wet etch rate for 1% HF in $H_2O$ solution is 0.5 Å/s. Film thickness before and after etch was used to calculate wet etch rate. Carbon and nitrogen concentration in the films were analyzed with Dynamic Secondary Ions Mass Spectrometry (SIMS) technique. The % non-uniformity was calculated from 6-point measurements using the following equation: % non-uniformity=((max−min)/(2*mean)). Film density was characterized with X-ray reflectometry (XRR). Table II summarizes $SiO_2$ films properties deposited with a fixed dose (8 seconds) of the DMATMS precursor at a wafer temperature ranging from 500 to 650° C.,

TABLE II

Silicon Oxide Film Properties Deposited with DMATMS

| Wafer temperature (Celcius) | Deposition Rate (Å/cycle) | Non-uniformity (%) | WER (Å/s) | C concentration (# of atoms/cc) | N concentration (# of atoms/cc) |
|---|---|---|---|---|---|
| 500 | 1.24 | 1.5 | 3.08 | 2.90E+19 | 1.68E+18 |
| 550 | 1.22 | 1.4 | NA | 3.82E+19 | 1.73E+18 |
| 600 | 1.25 | 0.8 | NA | 3.49E+19 | 2.49E+18 |
| 650 | 1.32 | 1.0 | 2.07 | 2.25E+19 | 2.51E+18 |

Film densities for silicon oxides deposited from DMATMS ranged from 2.08 to 2.23 g/cc.

Figure 3:
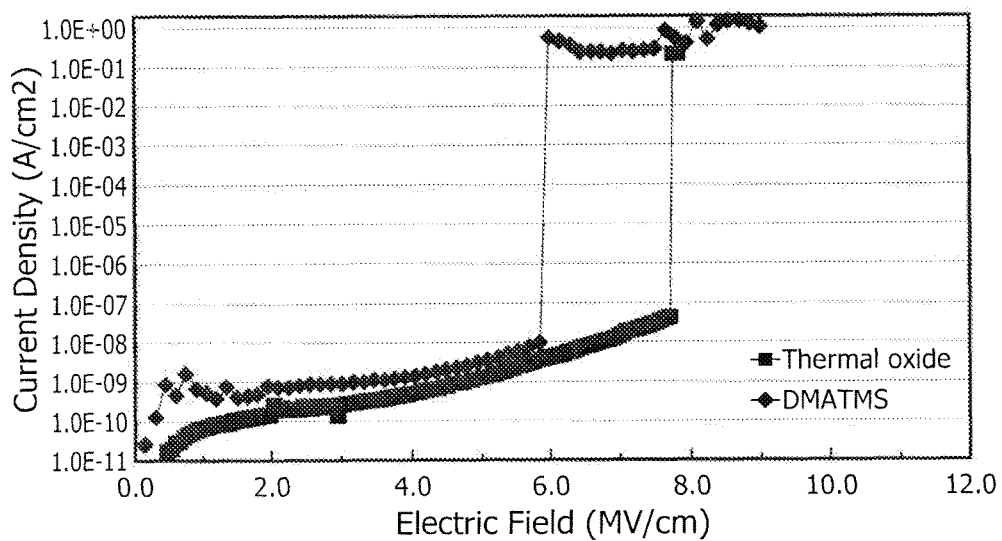
FIG. 3 provides current vs. electric field for $SiO_2$ films deposited at 650° C. with DMATMS vs. thermal oxide.

FIG. 3 depicts the leakage current and breakdown comparison between thermal oxide and $SiO_2$ deposited with DMATMS at 650° C. demonstrating that silicon oxide using DMATMS has electrical properties comparable to thermal oxide. Leakage current at 1-5 MV/cm, typical operating voltage, is within 1 order of magnitude of a thermal oxide typical device operating voltage.

To confirm ALD mode deposition, multiple precursor doses were used prior to introducing ozone to ensure that the deposition is self-limiting. Deposition steps are listed below in Table III:

TABLE III

ALD Conditions for Confirming ALD Mode Using DMATMS

| Step 1 | 6 sec | Evacuate reactor | <100 mT |
| Step 2a | 2 sec | Dose Silicon precursor | Reactor pressure typically <2 Torr |
| Step 2b | 2 sec | Evacuate reactor | <100 mT |
| Step 3 | 6 sec | Purge reactor with nitrogen | Flow 1.5 slpm $N_2$ |
| Step 4 | 6 sec | Evacuate reactor | <100 mT |
| Step 5 | 4 sec | Dose Ozone, 16-20% weight | |
| Step 6 | 6 sec | Purge reactor with nitrogen | Flow 1.5 slpm N2 |

Steps 2a and 2b were repeated to introduce multiple doses of silicon precursor. Both deposition rate and non-uniformity are reported in Table IV.

TABLE IV

Deposition Rates and Film Non-Uniformities of $SiO_2$ films deposited with multiple DMATMS doses

| Wafer temperature (Celcius) | DMATMS dose (seconds) | Deposition Rate (Å/cycle) | Non-uniformity (%) |
| --- | --- | --- | --- |
| 650 | 2 | 1.17 | 2.0 |
| 650 | 2 + 2 | 1.30 | 1.3 |
| 650 | 2 + 2 + 2 | 1.36 | 1.2 |

The deposition rates show self-limiting behavior and saturates with increasing precursor doses which confirms ALD mode deposition at 650° C.

Example 2: Atomic Layer Deposition of Silicon Oxide Films with Diethylaminotrimethylsilane Atomic layer deposition of silicon oxide films were conducted diethylaminotrimethylsilane (DEATMS) using steps listed in Table I of Example 1. Deposition rate and film non-uniformity of $SiO_2$ films deposited with DEATMS at 500-650° C. at a fixed precursor dose (8 seconds) are depicted in Table IV.

TABLE IV

Deposition Rate and Film Non-Uniformity of $SiO_2$ films deposited with fixed DEATMS dose

| Wafer temperature (Celcius) | Deposition Rate (Å/cycle) | Non-uniformity (%) |
| --- | --- | --- |
| 500 | 1.10 | 1.3 |
| 550 | 1.10 | 1.0 |
| 600 | 1.16 | 0.5 |
| 650 | 1.27 | 2.5 |

To confirm ALD mode deposition, multiple precursor doses were used prior to ozone deposition steps to ensure the deposition is self-limiting. Deposition steps are listed Table V below:

TABLE V

ALD Conditions for Confirming ALD Mode Using DEATMS

| Step 1 | 6 sec | Evacuate reactor | <100 mT |
| Step 2a | 2 sec | Dose Silicon precursor | Reactor pressure typically <2 Torr |
| Step 2b | 2 sec | Evacuate reactor | <100 mT |
| Step 3 | 6 sec | Purge reactor with nitrogen | Flow 1.5 slpm $N_2$ |
| Step 4 | 6 sec | Evacuate reactor | <100 mT |
| Step 5 | 4 sec | Dose Ozone, 16-20% weight | |
| Step 6 | 6 sec | Purge reactor with nitrogen | Flow 1.5 slpm $N_2$ |

Steps 2a and 2b are repeated to simulate multiple doses of silicon precursor. Both deposition rate and non-uniformity are reported in Table VI.

TABLE VI

Deposition Rate and Film Non-Uniformity of $SiO_2$ films deposited with multiple DEATMS dose

| Wafer temperature (Celcius) | Precursor dose (seconds) | Deposition Rate (Å/cycle) | Non-uniformity (%) |
| --- | --- | --- | --- |
| 650 | 2 | 1.01 | 2.3 |
| 650 | 2 + 2 | 1.20 | 2.8 |
| 650 | 2 + 2 + 2 | 1.30 | 2.5 |
| 650 | 2 + 2 + 2 + 2 | 1.35 | 2.5 |

The deposition rates show self-limiting behavior and saturates with increasing precursor doses which confirms ALD mode deposition at 650° C.

Example 3: Atomic Layer Deposition of Silicon Oxide Films on a Patterned Silicon Substrate with DMATMS $SiO_2$ film was deposited on patterned silicon wafers with DMATMS. The deposition process was performed using ozone as the oxygen source gas and precursor double pulse of 8 seconds at 650° C. The film deposited on the substrate was measured using field emission scanning electron microscopy (FESEM) Hitachi S-4800 SEM. The samples were mounted in cross-sectional holders and examined using SEM operated at 2 kV accelerating voltage. $SiO_2$ thickness measurements of sample cross-sections were taken at the top, the side wall, and the bottom of the trench. A review of the SEM cross-section of the $SiO_2$ film indicated excellent step coverage (>96%) and confirmed that the process is indeed an ALD process.

Example 4: Atomic Layer Deposition of Silicon Oxide Films with Diethylaminotriethylsilylane (DEATES)

Deposition of silicon oxide films were conducted using the silicon precursor diethylaminotriethylsilane (DEATES) and ozone. The deposition steps used are listed in Table I of Example 1. Table VII summarizes deposition rates and non-uniformities of $SiO_2$ films deposited at wafer temperatures of 500 to 650° C. using DEATES.

TABLE VII

Deposition Rates and Film Non-Uniformities of $SiO_2$ Films Deposited with Fixed DEATES Dose

| Wafer temperature (Celcius) | Deposition Rate (Å/cycle) | Non-uniformity (%) |
| --- | --- | --- |
| 500 | 0.91 | 1.44 |
| 550 | 0.97 | 1.1 |

TABLE VII-continued

Deposition Rates and Film Non-Uniformities of SiO$_2$ Films Deposited with Fixed DEATES Dose

| Wafer temperature (Celcius) | Deposition Rate (Å/cycle) | Non-uniformity (%) |
|---|---|---|
| 600 | 1.18 | 7.8 |
| 650 | 2.53 | 24.8 |

Referring to Table VII, the deposition rates and film non-uniformities increased at 600° C. which indicated some CVD reaction at 600° C. and a further increase in CVD reaction at 650° C.

Example 5: Atomic Layer Deposition of Silicon Oxide Films with Methoxytrimethylsilylane Atomic layers depositions of silicon oxide films were conducted using the silicon precursor methoxytrimethylsilylane. Depositions were performed using ozone at 650° C. with process steps listed in Table I of Example 1. The substrate temperature was set at 650° C. The deposition rate was about 0.3 Å/cycle.

Example 6: Atomic Layer Deposition of Silicon Oxide Films with Chlorotrimethylsilylane Atomic layers deposition of silicon oxide films was conducted using the silicon precursor chlorotrimethylsilylane. Depositions were performed using ozone as the oxygen source gas and the process parameters of the depositions are the same in Table I of Example 1. The substrate temperature was set at 650° C. The deposition rate was 0.5 Å/cycle.

Example 7: Atomic Layer Deposition of Silicon Oxide Films with Hexamethyldisilazane Atomic layers depositions of silicon oxide films were conducted using the silicon precursor hexamethyldisilane. Depositions were performed using ozone at 650° C. with process steps listed in Table I of Example 1. The deposition rate was about 1.3 Å/cycle.

Example 8: ALD Deposition of Silicon Oxide Film Using Bis(dimethylamino)dimethylsilane Bisdimethylaminodimethylsilane (BDMADMS) was used as the silicon precursor. BDMADMS has general structure of $R^1R^2{}_mSi(NR^3R^4)_n$, wherein $R^1$, $R^2$, $R^3$, $R^4$ are methyl, n=2, and m=1.

Depositions were performed on a laboratory scale ALD processing tool. Depositions were performed using ozone as the oxygen source gas and the process parameters of the depositions are the same in Table I.

Deposition rates and film non-uniformities of silicon oxide films deposited using BDMADMS with fixed precursor dose (8 seconds) at 500-650° C. are summarized in Table VIII:

TABLE VIII

Deposition Rate and Film Non-Uniformity of SiO$_2$ films deposited with fixed BDMADMS dose.

| Wafer temperature (Celcius) | Deposition Rate (Å/cycle) | Non-uniformity (%) |
|---|---|---|
| 300 | 0.67 | 2.1 |
| 500 | 0.96 | 2.1 |
| 650 | 1.72 | 5.0 |

Double precursor pulses process was used to further verify ALD mode. Table IX shows the deposition rate and non-uniformity of the films with single 8 sec pulse and double 8 second pulses.

TABLE IX

Summary of Process Parameters and Results for BDMADMS

| Wafer temperature (Celcius) | Precursor Pulse (seconds) | Deposition Rate (Å/cycle) | Non-uniformity (%) |
|---|---|---|---|
| 650 | 8 | 1.72 | 5.0 |
| 650 | 8 + 8 | 2.05 | 7.8 |

As Table IX shows, the deposition rate increased significantly when double precursor pulses were used and the uniformity decreased, which suggested some CVD mode deposition.

Example 9: Synthesis of 2,6-dimethylpiperidinotrimethylsilane

Figure 2:
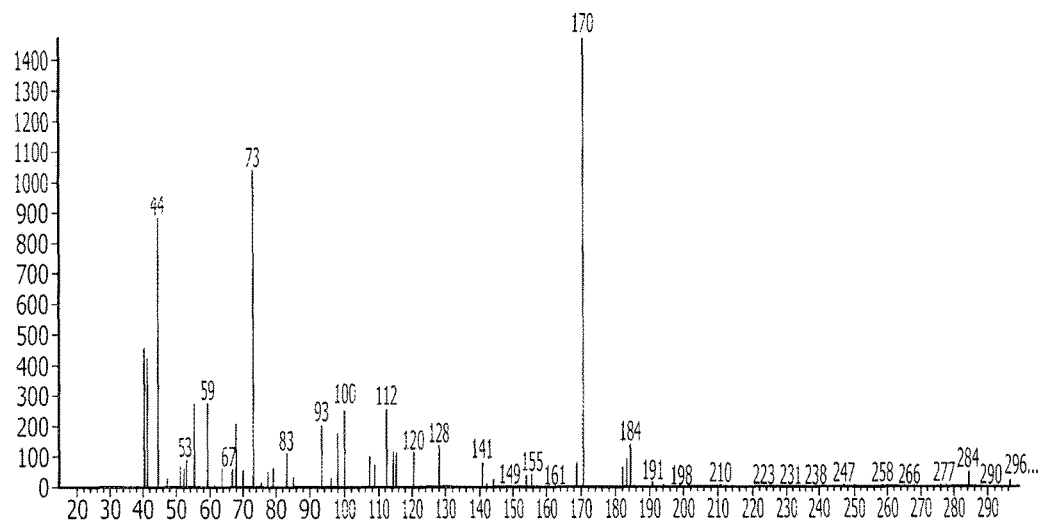
FIG. 2 provides a mass spectrum of 2,6-dimethylpiperidinotrimethylsilane.

In a 1000 ml three-necked round bottom flask equipped with an addition funnel, a condenser, and a mechanical stirrer, 113 g (1.0 mol) 2,6-dimethylpiperidine and 500 ml hexane were added. With stirring, 50.5 g (0.5 mol) chlorotrimethylsilane was added dropwise through the addition funnel. After the addition was completed, the reaction mixture was refluxed for 6 hours. Cooling down to room temperature, the mixture was filtered. The solid was washed with hexane, and the hexane solution was combined with the filtrate. Solvent hexane was removed by distillation. 134 g 2,6-dimethylpiperidinotrimethylsilane was obtained by fractional distillation. The yield was 75%. Mass spectrum provided in FIG. 2 confirmed that it is dimethylpiperidinotrimethylsilane with fragments at 185 (M), 170 (M-15).

The invention claimed is:

1. A process to deposit silicon oxide comprising the steps of:
   a. providing a substrate in a reactor;
   b. introducing into the reactor at least one silicon precursor;
   c. purging reactor with purge gas;
   d. introducing an oxygen source into the reactor; and
   e. purging reactor with purge gas; and
   wherein steps b through e are repeated until a desired thickness of silicon oxide is deposited;
   wherein the process is conducted at one or more temperatures ranging from over 600 to 800° C. and one or more pressures ranging from 50 miliTorr (mT) to 760 Torr; and
   wherein the at least one silicon precursor has a formula:

   $$R^1R^2{}_mSi(NR^3R^4)_nX_p \qquad \text{I.}$$

wherein $R^1$ is methyl; $R^2$ is methyl; $R^3$ is selected from hydrogen, a linear or branched $C_1$ to $C_{10}$ alkyl group, and a $C_6$ to $C_{10}$ aryl group; and $R^4$ is selected from, a linear or branched $C_1$ to $C_{10}$ alkyl group, a $C_6$ to $C_{10}$ aryl group, and a $C_3$ to $C_{10}$ alkylsilyl group, wherein $R^3$ and $R^4$ are linked to form a cyclic ring structure or $R^3$ and $R^4$ are not linked to form a cyclic ring structure X is a halide selected from the group consisting of Cl, Br and I, m is 2, n is 0 or 1, p is 0 or 1, and m+n+p=3.

2. The process of claim 1, wherein the at least one silicon precursor is selected from the group consisting of diethylaminotrimethylsilane, dimethylaminotrimethylsilane, ethylmethylaminotrimethylsilane, t-butylaminotrimethylsilane, iso-propylaminotrimethylsilane, di-isopropylaminotrimethylsilane, pyrrolidinotrimethylsilane, 2,6-dimethylpiperidinotrimethylsilane, and mixtures thereof.

3. The process of claim 1, wherein the at least one silicon precursor is selected from the group consisting of iso-propylaminotrimethylsilane, tert-butylaminotrimethylsilane, iso-butylaminotrimethylsilane, Cyclohexaminotrimethylsilane, pyrrolidinotrimethylsilane, 2-methylpyrrolidinotrimethylsilane, 2,5-dimethylpyrrolidinotrimethylsilane, piperidinotrimethylsilane, 2,6-dimethylpiperidinotrimethylsilane, 1-methylpiperazinotrimethylsilane, pyrrolyltrimethylsilane, 2,5-dimethylpyrrolyltrimethylsilane, imidazolyltrimethylsilane, 1,1,1,3,3,3-hexamethyldisilazane, and chlorotrimethylsilane.

4. The process of claim 1, wherein the pressure ranges from 50 miliTorr (mT) to 100 Torr.

5. The process of claim 1, wherein the purge gas is selected from the group consisting of nitrogen, helium and argon.

6. The process of claim 1, wherein the oxygen source is selected from the group consisting of oxygen, peroxide, oxygen plasma, water vapor, water vapor plasma, hydrogen peroxide, nitrous oxide and ozone source.

7. The process of claim 1, further comprising, after step e, the steps of:
   f. introducing water vapor or hydroxyl source into the reactor; and
   g. purging reactor with purge gas;
   wherein steps b through g are repeated until a desired thickness of silicon oxide is deposited.

8. The process of claim 2, further comprising, after step e, the steps of:
   f. introducing water vapor or hydroxyl source into the reactor; and
   g. purging reactor with purge gas;
   wherein steps b through g are repeated until a desired thickness of silicon oxide is deposited.

* * * * *